US010881319B2

(12) United States Patent
Suh et al.

(10) Patent No.: US 10,881,319 B2
(45) Date of Patent: Jan. 5, 2021

(54) APPARATUS FOR DIAGNOSING AND TREATING DIZZINESS

(71) Applicant: Seoul National University Hospital, Seoul (KR)

(72) Inventors: Myung-Whan Suh, Seoul (KR); Jun Ho Lee, Seoul (KR); Seung Ha Oh, Seoul (KR); Chiheon Kwon, Seoul (KR); Joong Woo Ahn, Seoul (KR); Yunseo Ku, Seoul (KR); Hee Chan Kim, Seoul (KR)

(73) Assignee: Seoul National University Hospital, Seoul (KR)

( * ) Notice: Subject to any disclaimer, the term of this patent is extended or adjusted under 35 U.S.C. 154(b) by 781 days.

(21) Appl. No.: 15/319,716

(22) PCT Filed: Jun. 15, 2015

(86) PCT No.: PCT/KR2015/005988
§ 371 (c)(1),
(2) Date: Nov. 15, 2017

(87) PCT Pub. No.: WO2015/194808
PCT Pub. Date: Dec. 23, 2015

(65) Prior Publication Data
US 2018/0049663 A1 Feb. 22, 2018

(30) Foreign Application Priority Data
Jun. 17, 2014 (KR) .......................... 10-2014-0073430

(51) Int. Cl.
*A61B 5/00* (2006.01)
*A61B 5/0496* (2006.01)
(Continued)

(52) U.S. Cl.
CPC .............. *A61B 5/0496* (2013.01); *A61B 5/05* (2013.01); *A61B 5/11* (2013.01); *A61B 3/113* (2013.01); *A61B 5/112* (2013.01); *A61B 5/1116* (2013.01)

(58) Field of Classification Search
CPC ..... A61B 3/113; A61B 5/4023; A61B 5/4863; A61B 5/11; A61B 5/6803; A61N 1/36036;
(Continued)

(56) References Cited

U.S. PATENT DOCUMENTS 7,490,611 B2 * 2/2009 Bromwich ........... A61B 5/1126
128/897
9,028,068 B2 * 5/2015 Chang .................... G02C 11/00
351/209
(Continued)

FOREIGN PATENT DOCUMENTS

JP 2001-198090 A 7/2001

OTHER PUBLICATIONS

Patent Cooperation Treaty, International Search Report and Written Opinion of the International Searching Authority, International Patent Application No. PCT/KR2015/005988, dated Sep. 14, 2015, 11 Pages (including English translation of International Search Report).

*Primary Examiner* — May A Abouelela
(74) *Attorney, Agent, or Firm* — Fenwick & West LLP (57) ABSTRACT

An apparatus for treating dizziness comprises an input unit configured to input a type of dizziness suffered by a patient, a storage unit configured to store different treatment methods respectively corresponding to different types of dizziness, an operation unit configured to search for a treatment method corresponding to the diagnosed type of dizziness among the treatment methods stored in the storage unit based on the diagnosed type of dizziness, and an output unit
(Continued)

configured to output the searched treatment method for the inputted type of dizziness to the patient.

12 Claims, 6 Drawing Sheets

(51) Int. Cl.
    *A61B 5/05*     (2006.01)
    *A61B 5/11*     (2006.01)
    *A61B 3/113*     (2006.01)

(58) Field of Classification Search
    CPC .................. A61N 2/002; G02B 27/017; G02B 2027/0187; G02B 2027/0138; G08B 21/0446; A61M 2210/0612
    USPC .................. 600/301, 558, 587, 595; 351/210
    See application file for complete search history.

(56) References Cited

U.S. PATENT DOCUMENTS

| | | |
|---|---|---|
| 2003/0116166 A1 | 6/2003 | Anthony |
| 2004/0097839 A1* | 5/2004 | Epley .................. A61B 5/0484 600/595 |
| 2007/0161875 A1* | 7/2007 | Epley .................. A61B 5/0484 600/301 |
| 2007/0261702 A1 | 11/2007 | Bromwich |
| 2007/0299362 A1* | 12/2007 | Epley .................. A61B 5/4863 600/559 |
| 2008/0058681 A1* | 3/2008 | Casali .................. A61B 3/0083 600/587 |
| 2010/0280372 A1* | 11/2010 | Poolman ............ A61B 5/04842 600/437 |
| 2011/0176106 A1 | 7/2011 | Lewkowski |
| 2011/0275959 A1* | 11/2011 | Casali .................. A61B 3/0083 600/595 |
| 2011/0282130 A1* | 11/2011 | Krueger ................ A61M 21/00 600/27 |
| 2012/0089049 A1 | 4/2012 | Suarez et al. |
| 2012/0133892 A1* | 5/2012 | Furman .................. A61B 3/113 351/210 |
| 2012/0316624 A1* | 12/2012 | Smith .................... A61N 2/006 607/99 |
| 2013/0296987 A1* | 11/2013 | Rogers .................... A61F 7/007 607/112 |
| 2015/0005587 A1* | 1/2015 | Qu ........................ A61B 5/4023 600/301 |
| 2015/0057233 A1* | 2/2015 | Dyhrfjeld-Johnsen ...................... A61K 38/13 514/20.5 |

* cited by examiner

APPARATUS FOR DIAGNOSING AND TREATING DIZZINESS

TECHNICAL FIELD

The present disclosure relates to an apparatus for diagnosing and treating dizziness and, more specifically, to a portable dizziness diagnosing and treating apparatus for diagnosing the type of dizziness on the basis of nystagmus, suggesting a treatment/alleviation method or a recurrence-preventing rehabilitation method depending on the type of diagnosed dizziness, and providing an evaluation as to whether a patient has accurately performed a treatment/rehabilitation exercise, on the basis of a re-measurement result of nystagmus of the patient or a sensing result of the motion of the patient when the patient has performed the treatment/rehabilitation exercise.

BACKGROUND

Dizziness is a term commonly designating all symptoms that make a patient feel as if the patient and the surrounding objects are moving even though they are stationary. Such dizziness may be largely classified into physiological dizziness and pathologic dizziness.

In most cases, the pathologic dizziness includes benign paroxysmal positional vertigo (hereinafter referred to as "BPPV") which is a disease caused when an otolith is deposited inside a semicircular duct of a human body, and vestibular neuritis (hereinafter referred to as "VN") which is a disease caused by inflammation generated in a vestibular nerve.

If BPPV or VN is generated, a patient feels intense dizziness to such an extent that a daily life becomes impossible. When dizziness occurs, an appropriate treatment/alleviation method may be provided depending on the type of dizziness. If a patient is able to perform such a treatment/alleviation method, the symptom of dizziness may be alleviated.

More specifically, a dizziness treatment/alleviation method varies depending on whether the type of dizziness is BPPV or VN. Particularly, if the type of dizziness is BPPV, the treatment varies depending on where an otolith exists in the semicircular ducts. For that reason, the dizziness treatment/alleviation method needs to be changed depending on the type of dizziness.

In this regard, the prior art is disclosed in Patent Document 1 (U.S. Pat. No. 7,490,611 issued on Feb. 17, 2009).

Patent Document 1 suggests a dizziness treatment/alleviation method. However, Patent Document 1 merely discloses an apparatus capable of providing a treatment method only when the type of dizziness is BPPV and the generation position of an otolith is specified. Patent Document 1 does not disclose an apparatus for changing a treatment/alleviation method depending on the type of dizziness.

Meanwhile, there may be a case where a patient diagnosed with dizziness receives a booklet which describes a rehabilitation method for preventing recurrence of dizziness. In order to effectively prevent recurrence of dizziness through such a rehabilitation method, a patient has to accurately locate and move the head and the body according to the rehabilitation method described in the booklet.

However, a patient is difficult to confirm whether the patient is accurately locating and moving the head and the body according to the rehabilitation method described in the booklet. Moreover, the old and the infirm are difficult to perform the rehabilitation method by themselves and may have a difficulty in learning the rehabilitation method through the booklet. Accordingly, a demand has existed for an apparatus or method capable of guiding a rehabilitation method to a patient in a more intuitive manner than a booklet and capable of evaluating and notifying, to a patient, whether the patient is accurately performing the rehabilitation method.

As mentioned above, the dizziness treatment/alleviation method varies depending on the type of dizziness. However, conventionally, the diagnosis for the type of dizziness is provided by a hospital in most cases. Thus, a patient suffering from dizziness could be diagnosed with the type of dizziness and guided with a treatment/alleviation method only when the patient visits a hospital while enduring the pain of dizziness. This makes it difficult to immediately cope with dizziness.

Under the circumstances, a demand has existed for a portable apparatus capable of immediately providing a diagnosis for the type of dizziness to a patient immediately upon occurrence of dizziness without requiring the patient to visit a hospital and capable of providing an appropriate treatment/alleviation method to the patient depending on the type of dizziness diagnosed.

SUMMARY

It is an object of the present disclosure to solve the aforementioned problems in their entirety.

Another object of the present disclosure is to provide a portable apparatus capable of providing a different treatment/alleviation method or a rehabilitation method depending on the type of dizziness for the prevention of recurrence of dizziness.

A further object of the present disclosure is to provide a portable apparatus capable of, when differently providing a treatment/alleviation method or a rehabilitation method, diagnosing the type of dizziness based on the symptom of dizziness currently suffered by a patient and differently providing a treatment/alleviation method or a rehabilitation method depending on the result of diagnosis.

A still further object of the present disclosure is to provide an apparatus capable of intuitively providing a dizziness treatment/alleviation method or a rehabilitation method to a patient.

A yet still further object of the present disclosure is to provide an apparatus capable of providing evaluation as to whether a patient has accurately performed a dizziness treatment/alleviation method or a rehabilitation method.

The features for achieving the above objects of the present disclosure are as follows.

In accordance with an aspect, there is provided an apparatus for treating dizziness, comprising: an input unit configured to input a type of dizziness suffered by a patient; a storage unit configured to store different treatment methods respectively corresponding to different types of dizziness; an operation unit configured to search for a treatment method corresponding to the inputted type of dizziness in the storage unit based on the inputted type of dizziness; and an output unit configured to output the searched treatment method for the inputted type of dizziness to the patient.

In accordance with an aspect, the output unit is configured to output the searched treatment method in the form of a voice, a photograph or moving images or in the form of a combination of at least two of the voice, the photograph and the moving images.

In accordance with an aspect, the apparatus for treating dizziness further comprises a motion sensing unit configured to sense a motion of the patient; and an evaluation unit configured to determine whether the motion of the patient sensed by the motion sensing unit is matched with a first motion suggested by the searched treatment method.

In accordance with an aspect, the motion sensing unit includes at least one of a gyro sensor and an acceleration sensor.

In accordance with an aspect, the output unit is configured to output a determination result of the evaluation unit.

In accordance with an aspect, the evaluation unit is configured to repeat determination until the motion of the patient sensed by the motion sensing unit is matched with the first motion, and the output unit is configured to output a result of the determination repeated by the evaluation unit.

In accordance with an aspect, the type of dizziness includes dizziness caused by vestibular neuritis and benign paroxysmal positional vertigo, and the benign paroxysmal positional vertigo is further classified based on a position of an otolith in a semicircular duct if the type of dizziness is the benign paroxysmal positional vertigo.

In accordance with another aspect, there is provided an apparatus for diagnosing and treating dizziness, comprising: a nystagmus detection unit configured to detect nystagmus from an eyeball of a patient suffering from dizziness; a diagnosis unit configured to diagnose a type of dizziness suffered by the patient based on the detected nystagmus; a storage unit configured to store different treatment methods respectively corresponding to different types of dizziness; an operation unit configured to search for a treatment method corresponding to the diagnosed type of dizziness among the treatment methods stored in the storage unit based on the diagnosed type of dizziness; and an output unit configured to output the searched treatment method for the diagnosed type of dizziness to the patient.

In accordance with another aspect, the nystagmus detection unit includes at least one electrode configured to measure a potential difference between a cornea and a retina of the eyeball.

In accordance with another aspect, the nystagmus detection unit includes an imaging means configured to take an image of a motion of the eyeball.

In accordance with another aspect, the apparatus for diagnosing and treating dizziness further comprises a motion sensing unit configured to sense a motion of the patient.

In accordance with another aspect, the diagnosis unit is configured to diagnose the type of dizziness based on the nystagmus and the motion of the patient.

In accordance with another aspect, the output unit is configured to output a first motion for nystagmus detection to the patient before the nystagmus is detected by the nystagmus detection unit.

In accordance with another aspect, the apparatus for diagnosing and treating dizziness further comprises a motion sensing unit configured to sense a motion of the patient; and an evaluation unit configured to determine whether the motion of the patient sensed by the motion sensing unit is matched with the first motion.

In accordance with another aspect, the output unit is configured to output a determination result of the evaluation unit.

In accordance with another aspect, the evaluation unit is configured to repeat determination until the motion of the patient sensed by the motion sensing unit is matched with the first motion, and the output unit is configured to output a result of the determination repeated by the evaluation unit.

In accordance with another aspect, the apparatus for diagnosing and treating dizziness further comprises an evaluation unit configured to evaluate whether the motion of the patient sensed by the motion sensing unit is matched with a second motion suggested by the searched treatment method.

In accordance with another aspect, the output unit is configured to output an evaluation result of the evaluation unit.

In accordance with another aspect, the evaluation unit is configured to repeat evaluation until the motion of the patient sensed by the motion sensing unit is matched with the second motion, and the output unit is configured to output a result of the evaluation repeated by the evaluation unit.

In accordance with another aspect, the nystagmus detection unit is configured to re-detect nystagmus from the patient after the searched treatment method is performed to the patient.

In accordance with another aspect, the apparatus for diagnosing and treating dizziness further comprises an evaluation unit configured to evaluate a treatment result of the searched treatment method performed to the patient based on the re-detected nystagmus, wherein the storage unit is configured to store at least one of the re-detected nystagmus and the treatment result of the searched treatment method.

In accordance with another aspect, the type of dizziness diagnosed by the diagnosis unit based on the nystagmus and the motion of the patient includes dizziness caused by vestibular neuritis and benign paroxysmal positional vertigo, and the benign paroxysmal positional vertigo is further classified based on a position of an otolith in a semicircular duct if the type of dizziness diagnosed by the diagnosis unit is the benign paroxysmal positional vertigo.

According to the present disclosure, a dizziness patient can be diagnosed with the type of dizziness immediately upon occurrence of dizziness and can be differently provided with a treatment/alleviation method or a rehabilitation method depending on the type of dizziness diagnosed. Furthermore, a dizziness patient can be intuitively provided with a dizziness treatment/alleviation method or a rehabilitation method and can be provided with evaluation as to whether a patient has accurately performed the dizziness treatment/alleviation method or the rehabilitation method.

DETAILED DESCRIPTION

Advantages, features and methods for achieving them will become apparent from the embodiments which will be described later in detail with reference to the accompanying drawings. However, the present disclosure is not limited to the embodiments described herein below but may be implemented in many different forms. The embodiments are provided to make complete the present disclosure and to completely inform the scope of the present disclosure to a person having an ordinary knowledge in the field to which the present disclosure pertains. The present disclosure is defined only by the claims.

In describing the embodiments of the present disclosure, the detailed descriptions of well-known functions or configurations will be omitted if it is determined that the detailed descriptions of well-known functions or configurations may unnecessarily make obscure the spirit of the present disclosure. The terms to be described later are defined in view of the functions exercised in the embodiments of the present disclosure and may vary depending on the intention of a user or an operator and the practice. Thus, the definition of terms shall be made based on the overall contents of the subject specification.

Embodiments of the present disclosure will now be described in detail with reference to the accompanying drawings.

Figure 1:
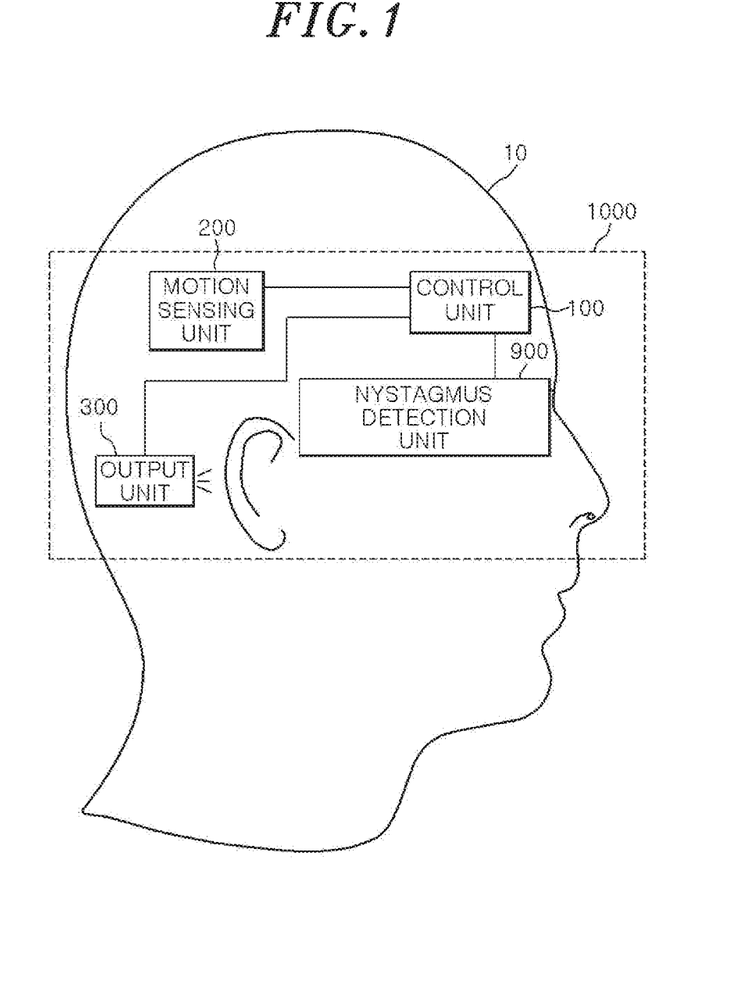
FIG. 1 is a view showing a state in which a patient wears an apparatus for diagnosing and treating dizziness according to a first embodiment of the present disclosure.

FIG. 1 is a view showing a state in which a patient wears an apparatus for diagnosing and treating dizziness according to a first embodiment of the present disclosure.

Referring to FIG. 1, an apparatus 1000 for diagnosing and treating dizziness according to a first embodiment of the present disclosure may have a form wearable by a patient 10. The patient may be provided with a diagnosis and dizziness treatment method through the apparatus 1000 when dizziness occurs.

More specifically, as shown in FIG. 1, the apparatus 1000 for diagnosing and treating dizziness may have a form which combines an eyeglass shape (or a goggle shape which will be referred to as "eyeglass shape" herein below) and a hearing aid shape. The configuration of the eyeglass shape may have a function of detecting nystagmus from the motion of an eyeball of the patient 10. The configuration of the hearing aid shape may have various functions such as a function of diagnosing the type of dizziness based on the detected nystagmus, a function of deriving a treatment/alleviation method or a rehabilitation method depending on the type of dizziness diagnosed and outputting the treatment/alleviation method or the rehabilitation method by a voice 301 or by other methods, a function of sensing the motion of the patient 10, a function of evaluating whether the motion of the patient 10 is matched with the motion suggested by the treatment/alleviation method or the rehabilitation method, and the like. If necessary, some or all of the functions of the configuration of the hearing aid shape may be performed by the configuration of the eyeglass shape.

In this regard, the first embodiment of the form which combines the eyeglass shape and the hearing aid shape shown in FIG. 1 is nothing more than one example. The idea of the present disclosure does not exclude other embodiments differing from the first embodiment. In other words, the idea of the present disclosure may include all types of embodiments differing from the one shown in FIG. 1, as long as the apparatus for diagnosing and treating dizziness is capable of detecting the nystagmus of the patient 10, diagnosing the type of dizziness based on the detected nystagmus and providing a treatment/alleviation method or a rehabilitation method. For example, the idea of the present disclosure may include an embodiment in which an eyeglass shape and a hearing aid shape are separated in hardware and connected in a wireless manner, an embodiment in which an eyeglass shape and a hairband shape are combined with each other, an embodiment which is realized by only an eyeglass shape (e.g., a Google glass form of Google, Inc.), or all types of other embodiments. Hereinafter, descriptions will be made on the basis of the first embodiment shown in FIG. 1.

The apparatus 1000 for diagnosing and treating dizziness shown in FIG. 1 may have a portable form. Thus, while not shown in FIG. 1, the apparatus 1000 for diagnosing and treating dizziness may include a power supply unit, such as a battery or the like, which is configured to supply electric power. Accordingly, immediately upon occurrence of dizziness, the patient 10 may be provided with a diagnosis for the type of dizziness using the apparatus 1000 for diagnosing and treating dizziness and may be provided with a treatment/alleviation method or a rehabilitation method corresponding to the type of dizziness.

Hereinafter, the configuration of the apparatus 1000 for diagnosing and treating dizziness according to the first embodiment of the present disclosure, which is shown in FIG. 1, will be conceptually described.

Figure 2A:
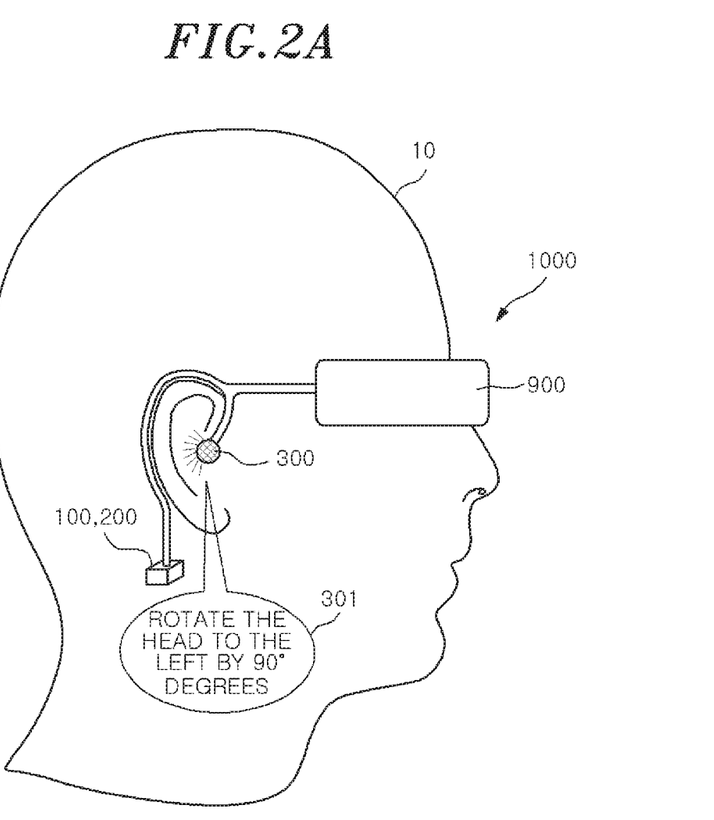
FIGS. 2A and 2B are block diagrams of the apparatus for diagnosing and treating dizziness according to the first embodiment of the present disclosure.
Figure 2B:
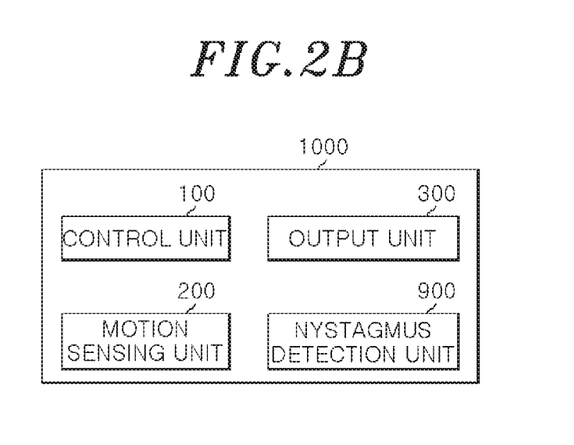

FIGS. 2A and 2B are block diagrams showing the configuration of the apparatus for diagnosing and treating dizziness according to the first embodiment of the present disclosure.

Referring to FIGS. 2A and 2B, the apparatus 1000 for diagnosing and treating dizziness according to the first embodiment of the present disclosure may include a nystagmus detection unit 900, a motion sensing unit 200, a control unit 100 or an output unit 300.

The nystagmus detection unit 900 may detect nystagmus and may transmit a nystagmus detection signal to the control unit 100. As described earlier, nystagmus refers to eyeball vibration. In a VN patient, horizontal rotatory direction fixed nystagmus is spontaneously generated regardless of the head position. In a BPPV patient, nystagmus is generated depending on the head posture with respect to the gravity direction. Accordingly, the detected nystagmus may be used for diagnosing the type of dizziness.

The detected nystagmus may be utilized as data for evaluating whether the patient 10 has accurately performed a treatment/rehabilitation exercise, namely the effect (result) of the treatment/rehabilitation exercise. More specifically, when the patient 10 performs a treatment/rehabilitation exercise according to the suggested treatment/alleviation method or the suggested rehabilitation method, the nystagmus detection unit 900 may re-detect nystagmus of the patient. The re-detected nystagmus may be provided to, for example, a doctor and may be utilized as data for evaluating the effect (result) of the treatment/rehabilitation exercise performed by the patient. However, the feature of re-detecting nystagmus may be a feature selectively performed in the first embodiment of the present disclosure.

Figure 4:
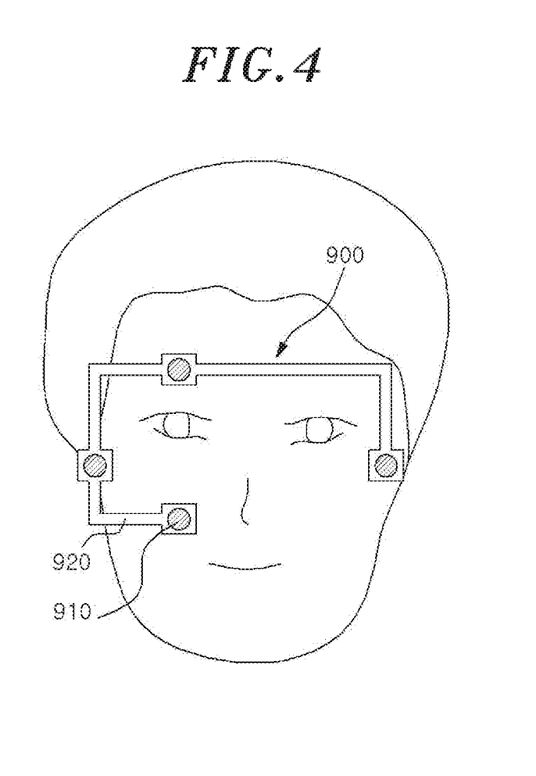
FIG. 4 is a view illustrating a nystagmus detection unit included in the apparatus for diagnosing and treating dizziness according to the first embodiment of the present disclosure.

In order to detect such nystagmus, as illustrated in FIG. 4, the nystagmus detection unit 900 may include a plurality of electrodes 910 disposed around the eyes of the patient 10. The nystagmus detection unit 900 may detect nystagmus by measuring a variation in potential difference between a cornea and a retina using the plurality of electrodes 910.

The method of detecting nystagmus by measuring a variation in potential difference between a cornea and a retina is called electronystagmography (ENG). Based on the result of the electronystagmography and the head position of the patient 10, it is possible to diagnose whether the type of dizziness is VN or BPPV and where an otolith is located in the semicircular ducts in the case of BPPV. In this regard, the technique of diagnosing the type of dizziness based on the result of the electronystagmography and the head position of the patient 10 is well-known in the art. Thus, the detailed description thereof will be omitted.

The nystagmus detection unit 900 including the plurality of electrodes 910 will now be described in detail. The electrodes 910 are connected by a connection portion 920 shown in FIG. 4 and may be included in the nystagmus detection unit 900 shown in FIG. 1. The electrodes 910 may be disposed around the eyes of the patient 10 so as to make contact with the skin of the patient 10 to measure a variation in potential difference between a cornea and a retina. However, the number of the electrodes 910, the positions of the electrodes 910 and the connection state of the electrodes 910 to the connection portion 920 are nothing more than exemplary ones. The present disclosure does not exclude a nystagmus detection unit including a plurality of electrodes differing from the above-described ones.

The nystagmus detection unit 900 including, as a configuration for nystagmus detection, the plurality of electrodes for electronystagmography as shown in FIG. 4 is nothing more than one example. The idea of the present disclosure does not exclude an embodiment differing from the above-described one. For example, the idea of the present disclosure may include an embodiment in which videonystagmography (VNG) for detecting nystagmus by capturing the motion of eyes as a video is applied to the nystagmus detection unit 900. To that end, the nystagmus detection unit 900 shown in FIG. 1 may include an imaging means configured to take images of the motion of eyes, which is not shown in the drawings. Even in the case of using the videonystagmography, similar to the case of using the electronystagmography, it is possible to diagnose whether the type of dizziness is VN or BPPV and where an otolith is located in the semicircular ducts in the case of BPPV. However, the technique of diagnosing the type of dizziness based on the result of the videonystagmography and the head position of the patient 10 is well-known in the art. Thus, the detailed description thereof will be omitted.

The motion sensing unit 200 may sense the motion of the patient 10 and may provide the sensed data to the control unit 100. For example, if the patient 10 has to take a specific motion prior to detecting nystagmus in order to diagnose the type of dizziness, the motion sensing unit 200 may sense the motion taken by the patient 10 and may provide data for the motion to the control unit 100. In the case where the patient 10 performs a dizziness treatment/alleviation method or a rehabilitation method, the motion sensing unit 200 may sense the motion of the patient 10 and may provide data for the motion to the control unit 100.

To that end, the motion sensing unit 200 may include a sensor capable of sensing the motion of the patient. For example, the motion sensing unit 200 may include a gyro sensor or an acceleration sensor. However, theses sensors are nothing more than exemplary ones. The idea of the present disclosure does not exclude the inclusion of other sensors.

The motion sensing unit 200 may sense, for example, the moving direction, the moving speed, the moving acceleration, the moving angle and the like of the patient using these sensors. In view of the fact that dizziness is correlated to the head motion of the patient 10, it is preferred that, as shown in FIG. 2A, the motion sensing unit 200 is located close to the head of the patient 10. For example, in the case of an embodiment of the apparatus 1000 for diagnosing and treating dizziness in which, unlike the first embodiment of the present disclosure, an eyeglass shape and a hearing aid shape are separated in hardware and connected in a wireless manner, it is preferred that the motion sensing unit 200 is included in the eyeglass shape relatively close to the head position. However, this is nothing more than one example. The idea of the present disclosure does not exclude an embodiment differing from the above-described one.

The output unit 300 may deliver a message on a motion to the patient 10. For example, if the patient 10 has to take a specific motion in order to diagnose the type of dizziness, the output unit 300 may output a message indicating a specific motion to the patient 10, or may output, to the patient 10, a message indicating whether the motion of the patient 10 is matched with the specific motion. In the case where the patient performs a dizziness treatment/alleviation method or a rehabilitation method, the output unit 300 may output, to the patient 10, a message indicating the motion suggested in the treatment/alleviation method or the rehabilitation method, or may output, to the patient 10, a message indicating whether the motion of the patient 10 is matched with the motion suggested in the treatment/alleviation method or the rehabilitation method.

In this regard, the message may have a form easily recognizable by the patient 10. In particular, it is preferred that the message has a form easily recognizable by the old and the infirm. For example, the message may be in the form of a voice, a photograph or moving images, or may be in the form of a combination of at least two of a voice, a photograph and moving images.

In the case where the message contains a voice, the output unit 300 may include a speaker as shown in FIG. 1. In the case where the message contains a photograph or moving images, the output unit 300 may include a display device (e.g., a small liquid crystal display or the like).

As in the form of the apparatus 1000 for diagnosing and treating dizziness shown in FIG. 1, the output unit 300 may be physically combined with other components included in the apparatus 1000 for diagnosing and treating dizziness. However, the idea of the present disclosure is not necessarily limited to this form as long as the message output from the output unit 300 can be easily recognized by the patient 10. For example, the output unit 300 may include a speaker or a display device and may be realized as an independent device separated from the apparatus 1000 for diagnosing and treating dizziness shown in FIG. 1.

The control unit 100 is configured to diagnose the type of dizziness of the patient 10 based on the nystagmus transferred from the nystagmus detection unit 900 and the motion of the patient transferred from the motion sensing unit 200, derive a treatment/alleviation method or a rehabilitation method depending on the type of dizziness diagnosed, notify the treatment/alleviation method or the rehabilitation method to the patient 10 through the output unit 300, evaluate whether the patient 10 has moved according to the treatment/alleviation method or the rehabilitation method, based on the motion of the patient 10 transferred from the motion sensing unit 200 and the nystagmus of the patient 10 re-detected by the nystagmus detection unit 900, and store an evaluation result to provide the evaluation result to a doctor later. Hereinafter, the control unit 100 will be described with reference to FIG. 3, which is a block diagram showing the control unit 100.

Figure 3:
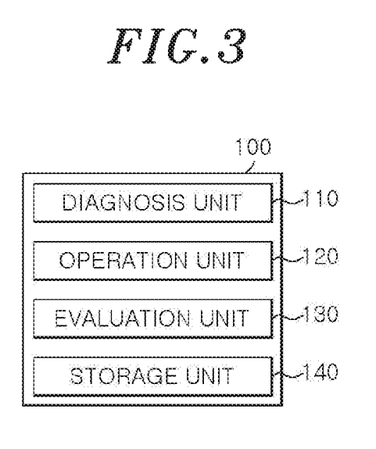
FIG. 3 is a block diagram of a control unit included in the apparatus for diagnosing and treating dizziness according to the first embodiment of the present disclosure.

The control unit 100 according to the first embodiment of the present disclosure may include a diagnosis unit 110, an operation unit 120, an evaluation unit 130 or a storage unit 140.

The control unit 100 may diagnose the type of dizziness of the patient 10 through the diagnosis unit 110. More specifically, the diagnosis unit 110 may diagnose the type of dizziness based on the nystagmus transferred from the nystagmus detection unit 900 shown in FIG. 2B and the motion of the patient 10 transferred from the motion sensing unit 200 shown in FIG. 2B.

For example, the diagnosis unit 110 may diagnose VN if horizontal rotatory direction fixed nystagmus is spontaneously generated regardless of the head position. The diagnosis unit 110 may diagnose BPPV if nystagmus is generated according to the head position transferred from the motion sensing unit 200 and may also diagnose the position of an otolith in the semicircular ducts based on the head position and the nystagmus.

To that end, a method for divisionally diagnosing the type of dizziness of the patient 10 based on the nystagmus and the head motion of the patient 10 is embodied in the diagnosis unit 110. In this regard, the method of diagnosing VN and BPPV based on the nystagmus and diagnosing the position of an otolith in the semicircular duct in the case of BPPV is well-known in the art. Thus, the detailed description thereof will be omitted herein.

Furthermore, the control unit 100 may derive a treatment/alleviation method or a rehabilitation method by receiving the type of dizziness diagnosed by the diagnosis unit 110. More specifically, the operation unit 120 included in the control unit 100 may search for and derive one of dizziness treatment/alleviation methods or rehabilitation methods stored in the storage unit 140, based on the type of dizziness inputted from the diagnosis unit 110. For example, if the diagnosis unit 110 diagnoses BPPV in which an otolith is generated in the posterior semicircular duct, the operation unit 120 may derive a head rotation direction or an upper body motion for treating or alleviating BPPV in which an otolith is generated in the posterior semicircular duct.

In this regard, the treatment/alleviation methods or the rehabilitation methods corresponding to the types of dizziness, which are stored in the storage unit 140, may be added, deleted and changed later.

Next, the control unit 100 may enable the motion according to the treatment/alleviation method or the rehabilitation method to be notified to the patient 10. If the patient 10 has to take a specific motion in order to diagnose the type of dizziness, the control unit 100 may enable the specific motion to be notified to the patient 10. To that end, the control unit 100 may control the output unit 300 so that the motion according to the treatment/alleviation method or the rehabilitation method or the specific motion to be taken by the patient 10 can be notified to the patient 10.

Furthermore, the control unit 100 may evaluate, through the evaluation unit 130, whether the patient 10 has moved according to the treatment/alleviation method or the rehabilitation method. The control unit 100 may enable the evaluation result of the evaluation unit 130 to be stored in the storage unit 140 so that the evaluation result can be provided to a doctor later.

More specifically, the evaluation unit 130 may evaluate the degree of dizziness alleviated according to the treatment/alleviation method or the rehabilitation method performed by the patient 10, namely the effect (result) of the treatment/alleviation method or the rehabilitation method performed by the patient 10, based on the re-detected nystagmus of the patient 10. In the case where the patient 10 has performed a treatment/rehabilitation exercise, the nystagmus detection unit 900 shown in FIG. 2B may re-detect the nystagmus of the patient 10 and the evaluation unit 130 may evaluate the effect (result) of the treatment/alleviation method or the rehabilitation method performed by the patient 10, based on the re-detected nystagmus. At this time, the nystagmus re-detected by the nystagmus detection unit 900 or the effect evaluated by the evaluation unit 130 may be stored in the storage unit 140.

Furthermore, the evaluation unit 130 included in the control unit 100 may determine whether the patient 10 has accurately moved according to the command. If the patient 10 has not accurately moved (not shown in FIG. 5), the control unit 100 may provide, through the output unit 300, a message indicating that the patient 10 has not accurately moved. In this regard, the message indicating that the patient 10 has not accurately moved may be repeatedly provided until, as a result of repeated determination of the motion of the patient 10, the evaluation unit 130 determines that the patient 10 has accurately moved. However, it is not necessarily required to perform the steps of determining the motion of the patient 10 with the evaluation unit 130 and outputting the determination result through the output unit 300.

In addition, if the patient 10 has to take a specific motion in order to diagnose the type of dizziness, the control unit 100 may determine, through the evaluation unit 130, whether the patient 10 has accurately moved according to the specific motion. More specifically, the evaluation unit 130 may determine whether the patient 10 has accurately moved according to the specific motion, by comparing the data on the motion of the patient 10 notified from the motion sensing unit 200 with the specific motion to be taken by the patient 10 in order to diagnose the type of dizziness.

In this regard, the determination result of the evaluation unit 130 may be provided to the patient 10 through the output unit 300 in real time, for example. That is to say, if the motion taken by the patient 10 according to the treatment/alleviation method or the rehabilitation method is not matched with the motion suggested by the treatment/alleviation method or the rehabilitation method, or if the motion taken by the patient 10 in order to diagnose the type of dizziness is not matched with the required motion, the evaluation unit 130 may notify the fact to the patient 10 through the output unit 300 in real time. Accordingly, the patient 10 may immediately receive feedback information as to whether the motion taken by the patient 10 is accurate and may have an opportunity of correcting the motion.

Providing the determination result of the evaluation unit 130 through the output unit 300 in real time is nothing more than one example. The idea of the present disclosure does not exclude providing the determination result of the evaluation unit 130 through the output unit 300 or through other methods at an arbitrary time such as a time specified by the patient 10, a time specified by a doctor or a pre-defined specific time.

While the foregoing description has been made on the premise that the control unit 100, the motion sensing unit 200, the output unit 300 and the nystagmus detection unit 900 included in the apparatus 1000 for diagnosing and treating dizziness according to the first embodiment of the present disclosure are combined into one hardware part, the first embodiment is nothing more than one example. The idea of the present disclosure does not exclude other embodiments differing from the first embodiment. That is to say, the idea of the present disclosure may include an embodiment in which the components of the apparatus for diagnosing and treating dizziness are separated into independent hardware parts which are connected through a wire/wireless communication network. For example, the idea of the present disclosure may include an embodiment in which the motion sensing unit and the nystagmus detection unit are combined into one hardware part, the output unit and the control unit are combined into another hardware part, and the respective hardware parts are connected through a wire/wireless communication network, and an embodiment in which the motion sensing unit, the nystagmus detection unit and the output unit are combined into one hardware part, only the control unit is provided as a separate hardware part, and the respective hardware parts are connected through a wire/wireless communication network. The following description will be made on the premise of the first embodiment in which the control unit, the motion sensing unit, the output unit and the nystagmus detection unit are combined into one hardware part.

Figure 5:
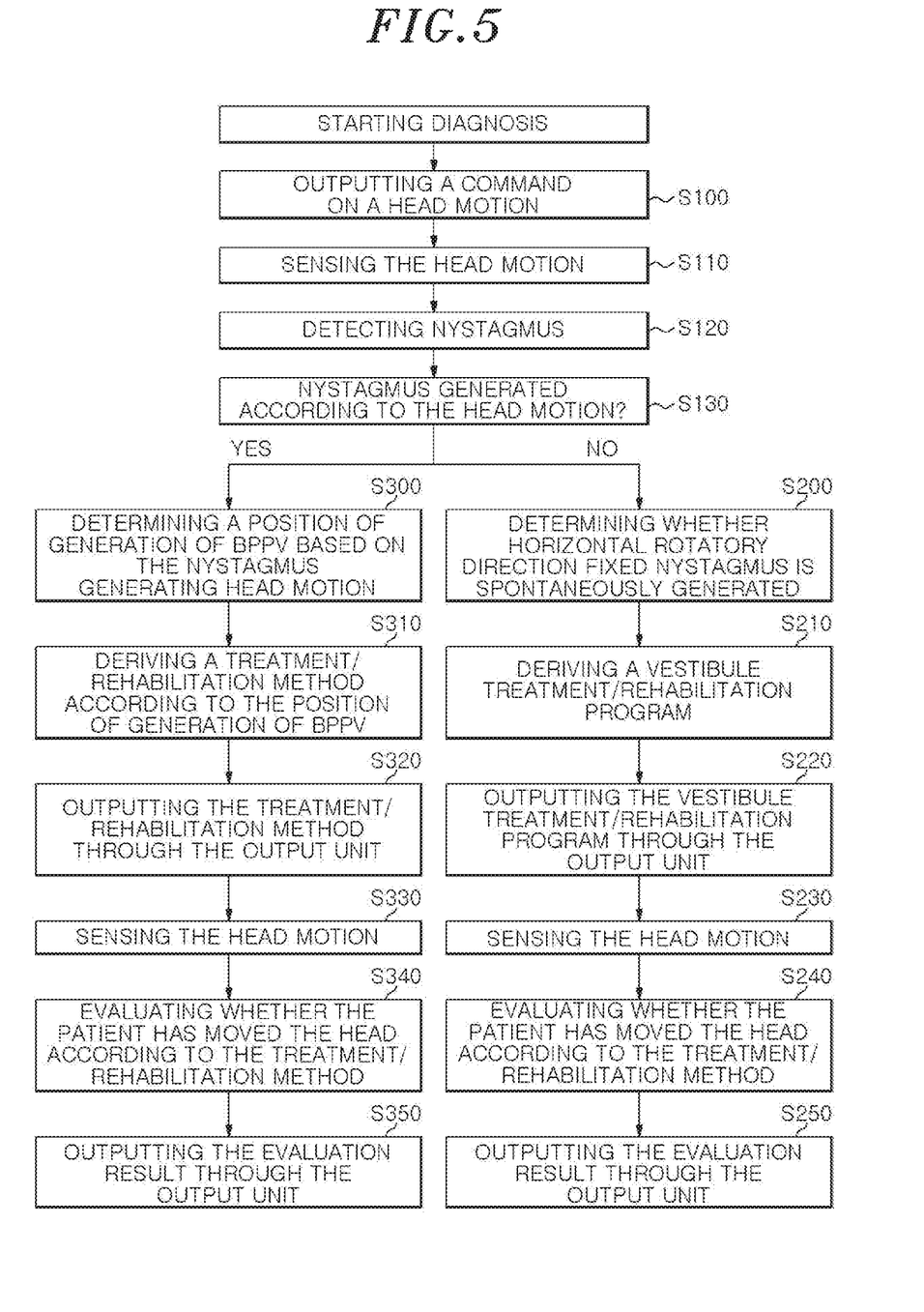
FIG. 5 is a control flowchart in the apparatus for diagnosing and treating dizziness according to the first embodiment of the present disclosure.
Figure 6:
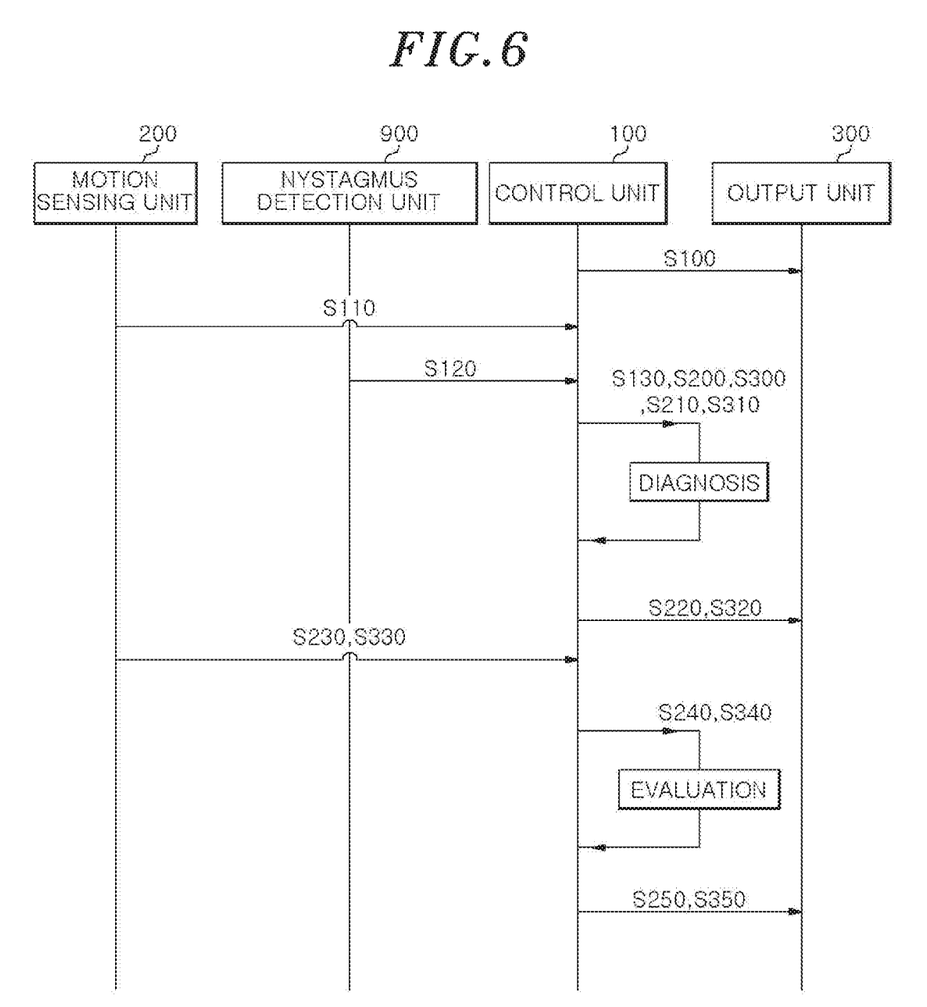
FIG. 6 is a control flowchart in the apparatus for diagnosing and treating dizziness according to the first embodiment of the present disclosure.

FIGS. 5 and 6 are control flowcharts in the apparatus for diagnosing and treating dizziness according to the first embodiment of the present disclosure.

Referring to FIGS. 5 and 6, when the patient 10 wears the apparatus 1000 for diagnosing and treating dizziness according to the first embodiment of the present disclosure, the control unit 100 may output a command on a head motion to the patient 10 through the output unit 300 in order to determine whether nystagmus is generated depending on the head position (S100). However, it is not necessarily required to perform the step of outputting such a command.

The motion sensing unit 200 may sense the motion of the patient 10 (especially, the head motion) and may provide information on the motion of the patient 10 to the control unit 100 (S110).

Furthermore, the evaluation unit 130 included in the control unit 100 may determine whether the patient 10 has accurately moved according to the command. If the patient 10 has not accurately moved (not shown in FIG. 5), the control unit 130 may provide, through the output unit 300, a message indicating that the patient 10 has not accurately moved. In this regard, the message indicating that the patient 10 has not accurately moved may be repeatedly provided until, as a result of repeated determination of the motion of the patient 10, the evaluation unit 130 determines that the patient 10 has accurately moved. However, it is not necessarily required to perform the steps of determining the motion of the patient 10 with the evaluation unit 130 and outputting the determination result through the output unit 300.

The nystagmus detection unit 900 may detect nystagmus from the patient 10 and may provide a detection result to the diagnosis unit 110 included in the control unit 100 (S120).

The diagnosis unit 110 may diagnose the type of dizziness of the patient 10 based on the nystagmus according to the motion of the patient 10 (S130). In this regard, the diagnosis unit 110 may diagnose VN if horizontal rotatory direction fixed nystagmus is spontaneously generated regardless of the head position (S200). The diagnosis unit 110 may diagnose BPPV if nystagmus is generated according to the head position transferred from the motion sensing unit 200 and may also diagnose the position of an otolith in the semicircular duct based on the head position and the nystagmus (S300).

The control unit 100 may provide the type of diagnosed dizziness to the patient 10 via the output unit 300. However, it is not necessarily required to perform such a step.

Furthermore, the operation unit 120 included in the control unit 100 may derive a treatment/alleviation method or a rehabilitation method based on the type of diagnosed dizziness (S210 or S310). The motion according to the treatment/alleviation method or the rehabilitation method thus derived may be provided to the patient 10 via the output unit 300 (S220 or S320).

Moreover, when the patient 10 takes a motion according to the treatment/alleviation method or the rehabilitation method, the motion sensing unit 200 may sense the motion and may transfer the sensed motion to the control unit 100 (S230 or S330).

In addition, the evaluation unit 130 included in the control unit 100 may evaluate whether the patient 10 has accurately moved according to the treatment/alleviation method or the rehabilitation method, by comparing data on the motion of the patient 10 transferred from the motion sensing unit 200 with the motion according to the treatment/alleviation method or the rehabilitation method derived by the operation unit 120 (S240 or S340). However, it is not necessarily required to perform the step of sensing the motion of the patient 10 and the step of evaluating the motion of the patient 10. Furthermore, the evaluation unit 130 may evaluate the effect (result) of the treatment/alleviation method or the rehabilitation method performed by the patient 10, based on the nystagmus of the patient 10 re-detected by the nystagmus detection unit 900. However, it is not necessarily required to perform such a step.

The evaluation result may be provided to the patient 10 via the output unit 300 (S250 or S350). In this regard, the evaluation result of the evaluation unit 130 may be provided through the output unit 300, for example, in real time. That is to say, if the motion taken by the patient 10 is not matched with the motion suggested by the treatment/alleviation method or the rehabilitation method, the evaluation unit 130 may notify the fact to the patient 10 through the output unit 300 in real time. Accordingly, the patient 10 may immediately receive feedback information on the accuracy of the motion taken by the patient 10 and may have an opportunity of correcting the motion. However, it is not necessarily required to perform such a step.

As described above, the apparatus for diagnosing and treating dizziness according to the first embodiment of the present disclosure includes the nystagmus detection unit 900. Nystagmus is detected from the patient 10 through the use of the nystagmus detection unit 900. The type of dizziness is diagnosed based on the detected nystagmus. The treatment/alleviation method or the rehabilitation method is differently provided depending on the type of diagnosed dizziness. However, the first embodiment is nothing more than one example. The idea of the present disclosure does not exclude other embodiments differing from the first embodiment. For example, the idea of the present disclosure may include a second embodiment in which the type of dizziness is inputted from the outside and the treatment/alleviation method or the rehabilitation method is differently provided depending on the type of inputted dizziness, unlike the first embodiment in which nystagmus is detected from the patient through the use of the nystagmus detection unit, the type of dizziness is diagnosed based on the nystagmus, and the treatment/alleviation method or the rehabilitation method is differently provided depending on the type of dizziness. In this case, the apparatus for diagnosing and treating dizziness according to the second embodiment may not include a nystagmus detection unit. Furthermore, the control unit included in the apparatus for diagnosing and treating dizziness according to the second embodiment may not include a diagnosis unit for diagnosing the type of dizziness and may further include a component (e.g., an input unit not shown in the drawings) for inputting the type of dizziness from the outside. Other configurations of the second embodiment may be the same as those of the first embodiment of the present disclosure. In addition, similar to the first embodiment of the present disclosure, the treatment/ alleviation method or the rehabilitation method is differently provided depending on the type of dizziness inputted from the outside.

As described above, according to the embodiments of the present disclosure, the dizziness patient can be diagnosed with the type of dizziness through the use of the portable dizziness diagnosing and treating apparatus immediately upon occurrence of dizziness and can be provided with a proper treatment/alleviation method or a proper rehabilitation method depending on the type of dizziness diagnosed. Furthermore, the dizziness patient can be more intuitively provided with the dizziness treatment/alleviation method or the rehabilitation method through the output unit included in the dizziness diagnosing and treating apparatus and can be provided with evaluation as to whether the patient has accurately performed the dizziness treatment/alleviation method or the rehabilitation method, through the evaluation unit and the output unit included in the dizziness diagnosing and treating apparatus.

The foregoing descriptions are nothing more than exemplary descriptions of the technical idea of the present disclosure. A person having an ordinary knowledge in the technical field to which the present disclosure pertains will be able to easily make different modifications and changes without departing from the essential characteristics of the present disclosure. Accordingly, the embodiments disclosed herein are not intended to limit the technical idea of the present disclosure but are intended to describe the technical idea of the present disclosure. The scope of the technical idea of the present disclosure shall not be limited by these embodiments. The protection scope of the present disclosure shall be construed based on the appended claims. All the technical ideas falling within the scope equivalent to the claims shall be construed to be included in the protection scope of the present disclosure.

What is claimed is:

1. An apparatus for diagnosing and treating dizziness, comprising:
    a nystagmus detection unit executed by a processor configured to detect nystagmus from an eyeball of a patient suffering from dizziness;
    a motion sensing unit configured to sense a motion of the patient;
    a diagnosis unit executed by the processor configured to diagnose a type of dizziness suffered by the patient based on the detected nystagmus and the sensed motion as one of vestibular neuritis and benign paroxysmal positional vertigo;
    a storage unit configured to store different treatment methods respectively corresponding to different types of dizziness;
    an operation unit executed by the processor configured to search for a treatment method corresponding to the diagnosed type of dizziness among the treatment methods stored in the storage unit based on the diagnosed type of dizziness; and
    an output unit configured to output the searched treatment method for the diagnosed type of dizziness to the patient,
    wherein the nystagmus detection unit includes at least one electrode configured to measure a potential difference between a cornea and a retina of the eyeball, and
    wherein the diagnosis unit obtains a location where an otolith is located among semicircular ducts of the patient based on the detected nystagmus and the sensed motion of the patient when the type of dizziness is the benign paroxysmal positional vertigo.

2. The apparatus of claim 1, wherein the nystagmus detection unit includes an imaging unit configured to take an image of a motion of the eyeball.

3. The apparatus of claim 1, wherein the output unit is configured to output a first motion to the patient, wherein the first motion indicates an action for the patient to take through which the type of dizziness suffered by the patient and the location where the otolith is located among the semicircular ducts of the patient are to be diagnosed.

4. The apparatus of claim 3, further comprising:
    an evaluation unit configured to determine whether the motion of the patient sensed by the motion sensing unit is matched with the first motion or not.

5. The apparatus of claim 4, wherein the output unit is configured to output a determination result of the evaluation unit.

6. The apparatus of claim 4, wherein the evaluation unit is configured to repeat determination until the motion of the patient sensed by the motion sensing unit is matched with the first motion, and the output unit is configured to output a result of the determination repeated by the evaluation unit.

7. The apparatus of claim 1, further comprising:
    an evaluation unit configured to determine whether the motion of the patient sensed by the motion sensing unit is matched with a second motion suggested by the searched treatment method or not, wherein the second motion indicates an action for the patient to take through which the dizziness treatment, alleviation or rehabilitation is to be achieved.

8. The apparatus of claim 7, wherein the output unit is configured to output an evaluation result of the evaluation unit.

9. The apparatus of claim 7, wherein the evaluation unit is configured to repeat evaluation until the motion of the patient sensed by the motion sensing unit is matched with the second motion, and the output unit is configured to output a result of the evaluation repeated by the evaluation unit.

10. The apparatus of claim 1, wherein the nystagmus detection unit is configured to re-detect nystagmus from the patient after the searched treatment method is performed to the patient.

11. The apparatus of claim 10, further comprising:
    an evaluation unit configured to evaluate a treatment result of the searched treatment method performed to the patient based on the re-detected nystagmus,
    wherein the storage unit is configured to store at least one of the re-detected nystagmus and the treatment result of the searched treatment method.

12. The apparatus of claim 1,
    wherein the output unit is configured to output a first motion for nystagmus detection to the patient before the nystagmus is detected by the nystagmus detection unit, the first motion indicating an action for the patient to take through which the type of dizziness suffered by the patient and the location where the otolith is located among the semicircular ducts of the patient are to be diagnosed,
    the apparatus further comprising:
    an evaluation unit executed by the processor configured to determine whether the motion of the patient sensed by the motion sensing unit is matched with the first motion or not,
    wherein in case the type of dizziness is the benign paroxysmal positional vertigo and the motion of the patient is matched with the first motion, the diagnosis unit determines that the otolith exists in one of the semicircular ducts corresponding to the first motion when the diagnosis unit receives one input that the dizziness of the patient has been alleviated, and wherein the diagnosis unit determines that the otolith exists in other semicircular ducts than said one of the semicircular ducts corresponding to the first motion when the diagnosis unit receives another input that the dizziness of the patient maintains without an improvement, and wherein the output unit outputs a second motion different from the first motion to the patient when the diagnosis unit determines that the otolith exists in other semicircular ducts than said one of the semicircular ducts corresponding to the first motion, the second motion indicating an action for the patient to take through which the dizziness treatment, alleviation or rehabilitation is to be achieved.

\* \* \* \* \*